US007482320B2

(12) United States Patent
Geesin et al.

(10) Patent No.: US 7,482,320 B2
(45) Date of Patent: Jan. 27, 2009

(54) MODULATION OF SMOOTH MUSCLE CELL PROLIFERATION

(75) Inventors: Jeffrey C. Geesin, Doylestone, PA (US);
Anna Gosiewska, Skillman, NJ (US);
Jean Xu, Hillsborough, NJ (US); Robert Gordon, Ixworth (GB); Jeff Yon, Ely (GB); Sridevi Naidu Dhanaraj, Raritan, NJ (US); Ian Harris, Belle Mead, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 418 days.

(21) Appl. No.: 10/471,221

(22) PCT Filed: Mar. 7, 2002

(86) PCT No.: PCT/EP02/02616

§ 371 (c)(1),
(2), (4) Date: Sep. 5, 2003

(87) PCT Pub. No.: WO02/072127

PCT Pub. Date: Sep. 19, 2002

(65) Prior Publication Data

US 2004/0142886 A1    Jul. 22, 2004

Related U.S. Application Data

(60) Provisional application No. 60/274,901, filed on Mar. 9, 2001.

(51) Int. Cl.
*A61K 38/18* (2006.01)
*C07K 14/475* (2006.01)

(52) U.S. Cl. .............................. 514/12; 514/2; 530/399

(58) Field of Classification Search ........................ None
See application file for complete search history.

(56) References Cited

FOREIGN PATENT DOCUMENTS

| WO | WO 99/47677 | 9/1999 |
| WO | WO 00/18212 | 4/2000 |
| WO | WO 00/34474 | 6/2000 |
| WO | WO 00/37641 | 6/2000 |
| WO | WO 00/59940 | 10/2000 |

OTHER PUBLICATIONS

International Search Report dated Feb. 24, 2003 for related application PCT/EP02/02616.
Li, Xuri et al. "PDGF-C is a new protease-activated ligand for the PDGF α-receptor", *Nature Cell Biology*, vol. 2, pp. 302-309 (2000).
Sun, Peter D. et al. "The cystine-knot growth-factor superfamily", *Annu. Rev. Biophys. Biomol. Struct.*, vol. 24, pp. 269-291 (1995).
Pötgens, Andy J.G. et al. "Covalent Dimerization of Vascular Permeability Factor/Vascular Endothelial Growth Factor Is Essential For Its Biological Activity", *J. Biol. Chem.* vol. 269, No. 52, pp. 32879-32885 (1994).
Andersson, Maria et al. "Assignment of Interchain Disulphide Bonds in Platelet-derived Growth Factor (PDGF) and Evidence for Agoninst Activity of Monomeric PDGF", *J. Biol. Chem.*, vol. 267, No. 16, pp. 11260-11266 (1992).
Heldin, Carl-Henrik et al. "Mechanism of Action and In Vivo Role of Platelet-Derived Growth Factor", *Physiological Reviews*, vol. 9, No. 4, pp. 1283-1316 (1999).
Lusis, Aldons J. "Atherosclerosis", *Nature*, vol. 407, pp. 233-241 (2000).
Mumtaz, F.H. et al. "Inhibition of diabetic bladder smooth muscle cell proliferation by endothelin receptor antagonists", *Urol Res*, vol. 28, pp. 254-259 (2000).
Devare, Sushilkumar G. et al. "Nucleotide Sequence of the Simian Sarcoma Virus Genome: Demonstration that its Acquired Cellular Sequences Encode the Transforming Gene Product p28 sis". *Proc. Natl. Acad. Sci*, USA, vol. 80, pp. 731-735 (1983).
Ferrara, Napoleone et al. "The Biology of Vascular Endothelial Growth Factor", *Endocrine Reviews*, vol. 18, No. 1, pp. 4-25 (1997).
Neufeld, Gera et al. "Vascular endothelial growth factor (VEGF) and its receptors", *FASEB J.*, vol. 13, pp. 9-22 (1999).
Soker, Shay et al. "Neuropilin-1 Is Expressed by Endothelial and Tumor Cells as an Isoform-Specific Receptor for Vascular Endothelial Growth Factor", *Cell*, vol. 92, pp. 735-745 (1998).
Berse, Brygida et al. "Vascular Permeability Factor (Vascular Endothelial Growth Factor) Gene is Expressed Differentially in Normal Tissues, Macrophages, and Tumors", *Mol. Biol. Cell*, vol. 3, pp. 211-220 (1992).
Takahashi, Y. et al. "Expression of Vascular Endothelial Growth Factor and Its Receptor, KDR, Correlates with Vascularity, Metastasis, and Proliferation of Human Colon Cancer[1]", *Cancer Research*, vol. 55, pp. 3964-3968 (1995).

(Continued)

*Primary Examiner*—Christine J Saoud
(74) *Attorney, Agent, or Firm*—Laura Donnelly

(57) ABSTRACT

There is provided a novel use for vascular endothelial growth factor, herein designated VEGF-X, and a CUB domain present in the sequence of VEGF-X, which enhance smooth muscle cell proliferation and can be used to treat diseases associated with reduced smooth muscle cell proliferation. VEGF-X, and a CUB domain can also be used in tissue engineering applications to increase the number of smooth muscle cells within specific tissue to restore that tissue function or architecture. Screening methods for identifying inhibitors of VEGF-X biological activity are also disclosed and these inhibitors include neutralizing VEGF-X antibodies, antisense VEGF-X sequences or non-protein antagonists competing with VEGF-X biological activity. Also provided are therapeutic methods for treating disorders associated with smooth muscle cells hyperproliferation and methods of diagnosis a pathological condition or susceptibility to a pathological condition associated with smooth muscle cell hyperproliferation.

2 Claims, 9 Drawing Sheets

OTHER PUBLICATIONS

Figure 3A:
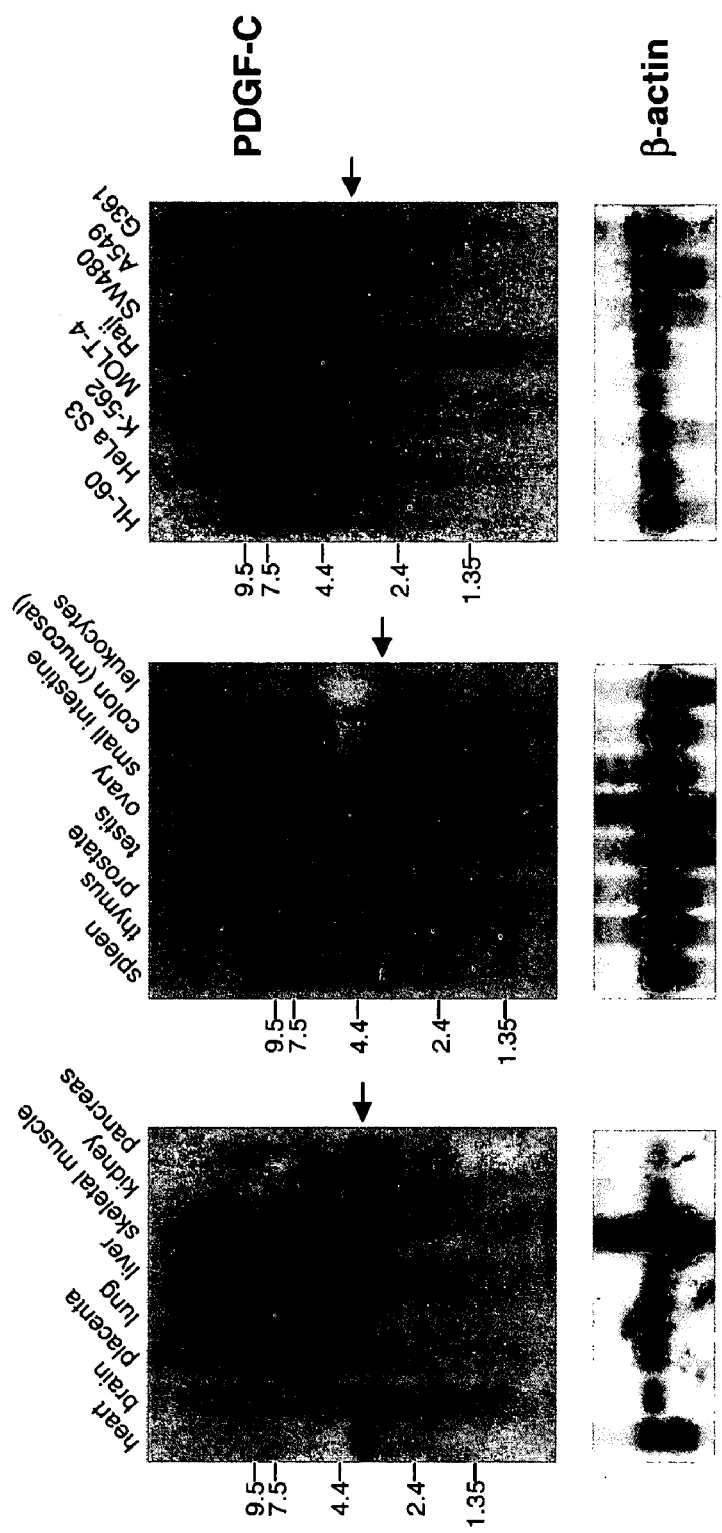

Kim, K. et al. "Inhibition of vascular endothelial growth factor-induced angiogenesis suppresses tumor growth in vivo", *Nature*, vol. 362, pp. 841-844 (1993).

Suzuki, J. et al. "Prevention of cardiac allograft arterosclerosis using antisense proliferating-cell nuclear antigen oligonucleotide[1]", *Transplantation*, vol. 70, No. 2, pp. 398-400 ((1999).

Folkman, J. "Angiogenesis in cancer, vascular, rheumatoid and other disease", *Nature Medicine*, vol. 1, No. 1, pp. 27-31 (1995).

Lagercrantz, J. et al.. "A comparative study of the expression patterns for *vegf, vegf-b/vrf* and *vegf-c* in the developing and adult mouse", *Biochem. Biophys. Acta*, vol. 1398, pp. 157-163 (1998).

Lee, J. et al. "Vascular endothelial growth factor-related protein: A ligand and specific activator of the tyrosine kinase receptor Flt4." *Proc. Natl. Acad. Sci.* USA, vol. 93, pp. 1988-1992 (1996).

Fitz, L. et al.. "Characterization of murine Flt4 ligand/VEGF-C", *Oncogene*, vol. 15, pp. 613-618 (1997).

Yamada, Y. et al. "Molecular Cloning of a Novel Vascular Endothelial Growth Factor, VEGF-D." *Genomics*, vol. 42, pp. 483-488 (1997).

Ausubel, F.M. et al. *Current Protocols in Molecular Biology*, John Wiley and Sons, Inc. pp. 1-3 (1997).

Masure, S. et al. "Molecular cloning, expression and tissue distribution of glial-cell-derived neurotrophic factor receptor α-3 (GFRα3)", *Eur. J. Biochem.*, vol. 251, pp. 622-630 (1998).

Heng, H. et al. "Modes of DAPI banding and simultaneous in situ hybridization", *Chromosoma*, vol. 102, pp. 325-332 (1993).

Robert, C. "Quantitative Image Analysis of Cell Proliferation After Balloon Catheter Injury in the Rabbit Carotid Artery", *Anal Quant Cytol Histol.*, vol. 17, No. 6, pp. 366-373 (1995).

Heng, H. et al. "High-resolution mapping of mammalian genes by in situ hybridization to free chromatin", *Proc. Natl. Acad. Sci.* USA, vol. 89, pp. 9509-9513 (1992).

Davies, M. et al. "Pathobiology of intimal hyperplasia", *British Journal of Surgery*, vol. 81, pp. 1254-1269 (1994).

Buschmann, M. et al. "Chodrocytes in Agarose Culture Synthesize a Mechanically Functional Extracellular Matrix", *Journal of Orthopaedic Research*, vol. 10, pp. 745-758 (1992).

Von Heijne, G. "A new method for predicting signal sequence cleavage sites", *Nucleic Acids Res.*, vol. 14, No. 11, pp. 4683-4690 (1986).

Bork, P. et al.. "The CUB Domain: A Widespread Module in Developmentally Regulated Proteins", *J. Mol. Biol.*, vol. 231, pp. 539-545 1993).

Tischer, E. et al. "The Human Gene for Vascular Endothelial Growth Factor: Multiple protein forms are encoded through alternative exon splicing", *J. Biol. Chem.*, vol. 266, No. 18, pp. 11947-11954 (1991).

Rocchigiani, M. et al. "Human *FIGF:* Cloning, Gene Structure, and Mapping to Chromosome Xp22.1 between the *PIGA* and the *GRPR* genes", *Genomics*, vol. 47, pp. 207-216 (1998).

Romero, A. "The crystal structures of two spermadhesins reveal the CUB domain fold", *Nature Structural Biology*, vol. 4, No. 10, pp. 783-788 (1997).

Paavonen, K. et al. "Novel Human Vascular Endothelial Growth Factor Genes VEGF-B and VEGF-C Localize to Chromosomes 11q13 and 4q34, Respectively", *Circulation*, vol. 93, pp. 1079-1082 (1996).

Stacker, S. et al. "Biosynthesis of Vascular Endothelial Growth Factor-D Involves Proteolytic Processing Which Generates Non-covalent Homodimers", *J. Biol. Chem.*, vol. 274, No. 45, pp. 32127-32136 (1999).

Makinen, T. et al. "Differential Binding of Vascular Endothelial Growth Factor B Splice and Proteolytic Isoforms to Neuropilin-1", *J. Biol. Chem.*, vol. 274, No. 30, pp. 21217-21222 (1999).

Bateman, A. et al. "The Pfam Protein Families Database", *Nucleic Acids Research*, vol. 28, No. 1, pp. 263-266 (2000).

Chancellor, M. et al. "Preliminary Results of Myoblast Injection Into the Urethra and Bladder Wall: A Possible Method for the Treatment of Stress Urinary Incontinence and Impaired Detrusor Contractility", *Neurology and Urodynamics*, vol. 19, pp. 279-287 (2000).

Gribskov, M. et al. "Profile Analysis: Detection of Distantly Related Proteins", *Proc. Natl. Acad. Sci.* USA, vol. 84, pp. 4355-4358 (1987).

Yokoyama, T. et al. "Myoblast therapy for stress urinary incontinence and bladder dysfunction", *World J. Urol.*, vol. 18, pp. 56-61 (2000).

Fig 1A

```
  1  TTTGTTTAAA CCTTGGGAAA CTGGTTCAGG TCCAGGTTTT GCTTTGATCC TTTTCAAAAA CTGGAGACAC AGAAGAGGGC
 81  TCTAGGAAAA AGTTTTGGAT GGGATTATGT GGAAACTACC CTGCGATTCT CTGCTGCCAG AGCAGGCTCG GCGCTTCCAC
161  CCCAGTGCAG CCTTCCCCTG GCGGTGGTGA AAGAGACTCG GGAGTCGCTG CTTCCAAAGT GCCCGCCGTG AGTGAGCTCT
                                                             M   S   L   F   G   L   L   L   L   T   S   A   L   A   G   Q   R   Q   G   T   Q
241  CACCCCCAGTC AGCCAAATGA GCCTCTTCGG GCTTCTCCCTG CTGACATCTG CCCTGGCCGG CCAGAGACAG GGGACTCAGG
      A   E   S   L   S   S   K   F   Q   F   S   S   N   K   E   Q   N   G   V   Q   D   P   Q   H   E   R
321  CGGAATCCAA CCTGAGTAGT AAATTCCAGT TTTCCAGCAA CAAGGAACAG AACGGAGTAC AAGATCCTCA GCATGAGAGA
      I   I   T   V   S   T   N   G   S   I   H   S   P   R   F   F   P   H   T   Y   P   R   N   T   V   L   V   W
401  ATTATTACTG TGTCTACTAA CGGAAGTATT CACAGCCCAA GGTTTCCTCA TACTTATCCA AGAAATACGG TCTTGGTATG
      R   L   V   A   V   E   E   N   V   W   I   Q   L   T   F   D   E   R   F   G   L   E   D   P   E   D
481  GAGATTAGTA GCAGTAGAGG AAAATGTATG GATACAACTT ACGTTTGATG AAAGATTTGG GCTTGAAGAC CCAGAAGATG
      D   I   C   K   Y   D   F   V   E   V   E   E   P   S   D   G   T   I   L   G   R   W   C   G   S   G   T
561  ACATATGCAA GTATGATTTT GTAGAAGTTG AGGAACCCAG TGATGGAACT ATATTAGGGC GCTGGTGTGG TTCTGGTACT
      V   P   G   K   Q   I   S   K   G   N   Q   I   R   I   R   F   V   S   D   E   Y   F   P   S   E   P   G
641  GTACCAGGAA AACAGATTTC TAAAGGAAAT CAAATTAGGA TAAGATTTGT ATCTGATGAA TATTTTCCTT CTGAACCAGG
      F   C   I   H   Y   N   I   V   M   P   Q   F   T   E   A   V   S   P   S   V   L   P   P   S   A   L
721  GTTCTGCATC CACTACAACA TTGTCATGCC ACAATTCACA GAAGCTGTGA GTCCTTCAGT GCTACCCCCT TCAGCTTTGC
      P   L   D   L   N   N   A   I   T   A   F   S   T   L   E   D   L   I   R   Y   L   E   P   E   R   W
801  CACTGGACCT GCTTAATAAT GCTATAACTG CCTTTAGTAC CTTGGAAGAC CTTATTCGAT ATCTTGAACC AGAGAGATGG
      Q   L   D   L   E   D   L   Y   R   P   T   W   Q   L   L   G   K   A   F   V   F   G   R   K   S   R   V
881  CAGTTGGACT TAGAAGATCT ATATAGGCCA ACTTGGCAAC ACTTCTTGGCAA GGCTTTTGTT TTTGGAAGAA AATCCAGAGT
      V   D   L   N   L   L   T   E   E   V   R   L   Y   S   C   T   P   R   N   F   S   V   S   I   R   E
961  GGTGGATCTG AACCTTCTAA CAGAGGAGGT AAGATTATAC AGCTGCACAC CTCGTAACTT CTCAGTGTCC ATAAGGAAAG
```

Fig 1A Continued

```
        E   L   K   R       T   D   T       I   F   W   P       G   C   L       L   V   K   R   C   G   G       N   C   A   C   C   L
1041   AACTAAAGAG AACCGATACC ATTTTCTGGC CAGGTGTCT CCTGGTTGTCT CGCTGTGGTG GGAACTGTGC CTGTTGTCTC

H   N   C   N   E   C   Q       C   V   P       S   K   V   T   ▼ K   K   Y       H   E   V       L   Q   L   R   P   K   T
1121   CACAATTGCA ATGAATGTCA ATGTGTCCCA AGCAAAGTTA CTAAAAAATA CCACGAGTC CTTCAGTTGA GACCAAAGAC

G   V   R       G   L   H   K   S   L   T       D   V   A       L   E   H   H   E   E   C       D   C   V       C   R       G
1201   CGGTGTCAGG GGATTGCACA AATCACTCAC CGACGTGGCC CTGGAGCACC ATGAGGAGTG TGACTGTGTG TGCAGAGGGA

S   T   G   G
1281   GCACAGGAGG ATAGCCGCAT CACCACCAGC AGCTCTTGCC CAGAGCTGTG CAGTGCAGTG GCTGATTCTA TTAGAGAACG
1361   TATGCGTTAT CTCCATCCTT AATCTCAGTT GTTTGCTTCA AGGACCTTTC ATCTTCAGGA TTTACAGTGC ATTCTGAAAG
1441   AGGAGACATC AAACAGAATT AGGAGTTGTG CAACAGCTCT TTTGAGAGGA GGCCTAAAGG ACAGGAGAAA AGGTCTTCAA
1521   TCGTGGAAAG AAAATTAAAT GTTGTATTAA ATAGATCACC AGCTAGTTTC AGAGTTACCA TGTACGTATT CCACTAGCTG
1601   GGTTCTGTAT TTCAGTTCTT TCGATACGGC TTAGGGTAAT GTCAGTACAG GAAAAAAACT GTGCAAGTGA GCACCTGATT
1681   CCGTTGCCTT GCTTAACTCT AAAGCTCCAT GTCCTGGGCC TAAAATCGTA TAAAATCTGG ATTTTTTTTT TTTTTTTTTG
1761   CTCATATTCA CATATGTAAA CCAGAACATT CTATGTACTA GATTTTTCAT ATTTCTTATT TTTTAAAAAG GAACTATGTT GCTATGAATT
1841   AAACTTGTGT CATGCTGATA GGACAGACTG AAAGAAGAGT GGCCTTATCT TCACTTTATC GATAAGTCAG GAAGAGAACT
1921   ACATTCATGG TTTGAAGAG ATAAACCTGA TTCTCCTTTT GACATTATAA CTGTTGGCTT TTCTAATCTT GTTAAATATA TCTATTTTTA
2001   TCATTGTGTA CATTTTATA TTAATATTCT TTTTTATGAC AACTTAGATC AACTATTTT AGCTTGGTAA ATTTTCTAA ACACAATTGT
2081   CCAAAGGTAT TTAATATTCT TTTTTATGAC AACTTAGATC AACTATTTT AGCTTGGTAA TACATGTATT TCATTCTCGT ATGGTGCTAG
2161   TATAGCCAGA GGAACAAAGA TGATATAAAA TATTGTTGCT CTGACAAAAA GTTGCAAAGA CTTTTTGAAA ATAATTAAAT
2241   AGTTAGATTA ATCTGCATTT TAAAAAAACTG AATTGGAATA TGAAAATAAA AAGCAACTTA TGAAAGTAGA CATTCAGATC CAGCCATTAC
2321   TATCATATCT TCCATTCCTG TTATTGGAGA CCTAGCTCAG AAAACATAA AGCACCTTGA AAAGACTTG GCAGCTTCCT
2401   TAACCTATTC CTTTTTTGGG GAAATCTGAG CCTAGCTCAG CACATCCTAT TTATTGTGAT GTTGTGGTTT TATTATCTTA AACTCTGTTC
2481   GATAAAGCGT GCTGTGCTGT GCAGTAGGAA CACATCCTAT TTATTGTGAT GTTGTGGTTT TATTATCTTA AACTCTGTTC
2561   CATACACTTG TATAAATACA TGGATATTTT TATGTACAGA AGTATGTCTC TTAACCAGTT CACTTATTGT AC
```

Fig 1B

```
PDGF-C        : MSLFGLLLLTSALAGQRQGTQAESNLSSKFQFSSNKEQNGVQDPQHERIITVSTNGSIHS :  60

PDGF-C        : PRFPHTYPRNTVLVWRLVAVEENVWIQLTFDERFGLEDPEDDICKYDFVEVEEPSDGTIL : 120

PDGF-C        : GRWCGSGTVPGKQISKGNQIRIRFVSDEYFPSEPGFCIHYNIVMPQFTEAVSPSVLPPSA : 180
var 1         : ..IRFVSDEYFPSEPGFCIHYNIVMPQFTEAVSPSVLPPSA : 180
var 2         : ..IRFVSDEYFPSEPSNRGGKIIQLHTS*             : 167

PDGF-C        : LPLDLLNNAITAFSTLEDLIRYLEPERWQLDLEDLYRPTWQLLGKAFVFGRKSRVVDLNL : 240
var 1         : LPLDLLNNAITAFSTLEDLIRYLEPERWQLDLEDLYRPTWQLLGKAFVFGRKSRVVDLNL : 240

PDGF-C        : LTEEVRLYSCTPRNFSVSIREELKRTDTIFWPGCLLVKRCGGNCACCLHNCNECQCVPSK : 300
var 1         : LTEE------------------------------------------------------- : 243

PDGF-C        : VTKKYHEVLQLRPKTGVRGLHKSLTDVALEHHEECDCVCRGSTGG* : 345
var 1         : ------VLQLRPKTGVRGLHKSLTDVALEHHEECDCVCRGSTGG* : 282
```

Fig 2A

```
PLGF : CRALERLVDVVSEYPSEVEHMFS--PSCVSLLRCTG---CC--GDEDLHC
VEGF : CHPIETLVDIFQEYPDEIEYIFK--PSCVPLMRCGG---CC--NDEGLEC
VEGB : CQPREVVVPLTVELMGTVAKQLV--PSCVTVQRCGG---CC--PDDGLEC
VEGC : CMPREVCIDVGKEFGVATNTFFK--PPCVSVYRCGG---CC--NSEGLQC
VEGD : CSPRETCVEVASELGKSTNTFFK--PPCVNVFRCGG---CC--NEESLIC
PDGA : CKTRTVIYEIPRSQVDPTSANFLIWPPCVEVKRCTG---CC--NTSSVKC
PDGB : CKTRTEVFEISRRLIDRTNANFLVWPPCVEVQRCSG---CC--NNRNVQC
PDGC : CTPRNFSVSIREEL-KRTDTIFW--PGCLLVKRCGGNCACCLHNCNECQC

PLGF : VPVETANVTMQLLKIRS-----GDRPSYVELTFSQHVRCEC
VEGF : VPTEESNITMQIMRIKP-----HQGQHIGEMSFLQHNKCEC
VEGB : VPTGQHQVRMQILMIR------YPSSQLGEMSLEEHSQCEC
VEGC : MNTSTSYLSKTLFEITVP---LSQGPKPVTISFANHTSCRC
VEGD : MNTSTSYISKQLFEISVP---LTSVPELVPVKVANHTGCKC
PDGA : QPSRVHHRSVKVAKVEYVR--KKPKLKEVQVRLEEHLECAC
PDGB : RPTQVQLRPVQVRKIEIVR--KKPIFKKATVTLEDHLACKC
PDGC : VPSKVTKKYHEVLQLRPKTGVRGLHKSLTDVALEHHEECDC
```

Fig 2B

```
BMP1_HUMAN : CGETLQ-DSTGNFSSPEYPNGYSAHMHCVWRISVTPGEK-IILNFTSLDL
BMP1_XENLA : CGGEVK-KDSCHIQSPNYPDDYRPNKACVWKLSVSEGFH-VGISFQSFEI
NRP_CHICK  : CGDTIKILSPGYLTSPGYPQSYHPSQKCEWLIQAPEPYQRIMINFNPHFD
NRP_MOUSE  : CGGTIKIENPGYLTSPGYPHSYHPSEKCEWLIQAPEPYQRIIINFNPHFD
NRP_XENLA  : CGDTIKITSPSYLTSAGYPHSYPPSQRCEWLIQAPEHYQRIMINFNPHFD
PDGFC      : HERIITVSTNGSIHSPRFPHTYPRNTVLVWRLVAVEENVWIQLTFDERFG

BMP1_HUMAN : YRS---RLCWYDYVEVRDGFWRKAPLRGRFCGS-KLPEPIVSTDSRLWVE
BMP1_XENLA : ERH---DSCAYDYLEIRDGSSETSPLVGRFCGY-DKPDDIKSSTNQLWIK
NRP_CHICK  : LED---RDCKYDYVEVIDGDNAEGRLWGKYCGK-IAPPPLVSSGPYLFIK
NRP_MOUSE  : LED---RDCKYDYVEVIDGENEGGRLWGKFCGK-IAPSPVVSSGPFLFIK
NRP_XENLA  : LED---RECKYDYVEVIDGDNANGQLLGKYCGK-IAPSPLVSTGPSIFIR
PDGFC      : LEDPEDDICKYDFVEVEEPS--DGTILGRWCGSGTVPGKQISKGNQIRIR

BMP1_HUMAN : FRSSSNWVGK-GFFAVYP
BMP1_XENLA : FVSDGSINKA-GFSLNYP
NRP_CHICK  : FVSDYETHGA-GFSIRYP
NRP_MOUSE  : FVSDYETHGA-GFSIRYP
NRP_XENLA  : FVSDYETPGA-GFSIRYP
PDGFC      : FVSDEYFPSEPGFCIHYN
```

Fig 4
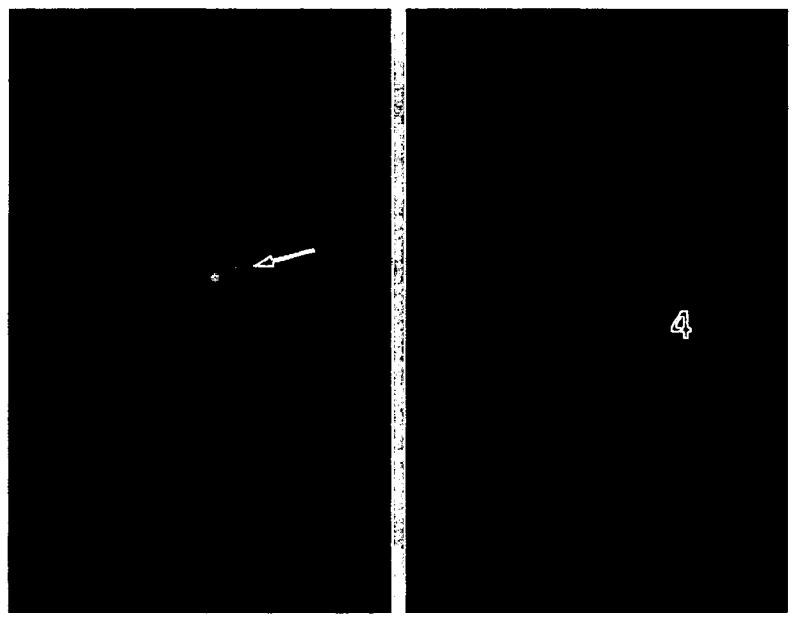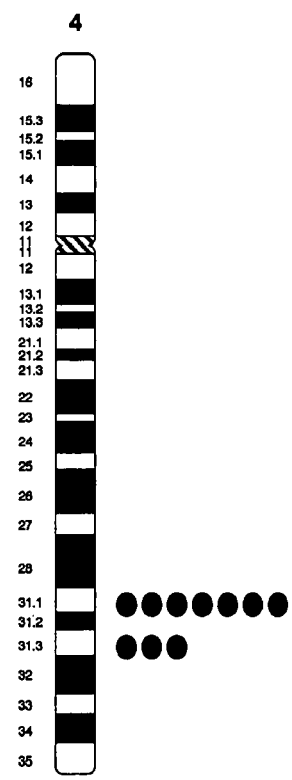

Fig 5
Fig 5A
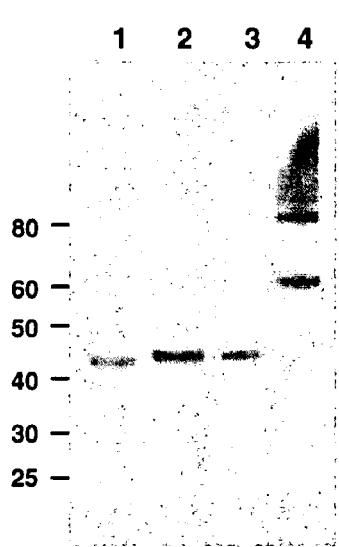
Fig 5B
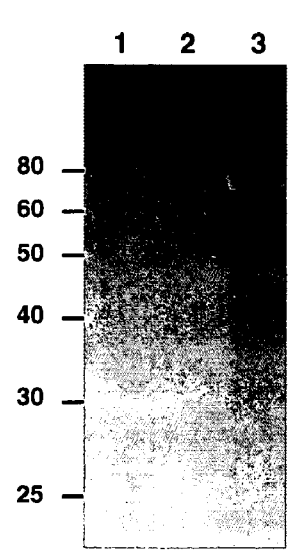
Fig 5C
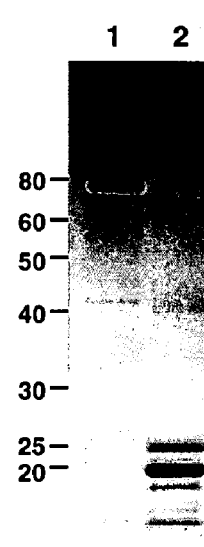

```
                         SEQUENCE LISTING

<160> NUMBER OF SEQ ID NOS: 6

<210> SEQ ID NO 1
<211> LENGTH: 345
<212> TYPE: PRT
<213> ORGANISM: Homo sapiens

<400> SEQUENCE: 1

Met Ser Leu Phe Gly Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
                20                  25                  30

Ser Ser Asn Lys Glu Gln Asn Gly Val Gln Asp Pro Gln His Glu Arg
            35                  40                  45

Ile Ile Thr Val Ser Thr Asn Gly Ser Ile His Ser Pro Arg Phe Pro
        50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270
```

```
Gly Cys Leu Leu Val Lys Arg Cys Gly Gly Asn Cys Ala Cys Cys Leu
            275                 280                 285

His Asn Cys Asn Glu Cys Gln Cys Val Pro Ser Lys Val Thr Lys Lys
        290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
                340                 345

<210> SEQ ID NO 2
<211> LENGTH: 111
<212> TYPE: PRT
<213> ORGANISM: Homo sapiens

<400> SEQUENCE: 2

Gly Val Gln Asp Pro Gln His Glu Arg Ile Ile Thr Val Ser Thr Asn
1               5                   10                  15

Gly Ser Ile His Ser Pro Arg Phe Pro His Thr Tyr Pro Arg Asn Thr
            20                  25                  30

Val Leu Val Trp Arg Leu Val Ala Val Glu Glu Asn Val Trp Ile Gln
        35                  40                  45

Leu Thr Phe Asp Glu Arg Phe Gly Leu Glu Asp Pro Glu Asp Asp Ile
    50                  55                  60

Cys Lys Tyr Asp Phe Val Glu Val Glu Glu Pro Ser Asp Gly Thr Ile
65                  70                  75                  80

Leu Gly Arg Trp Cys Gly Ser Gly Thr Val Pro Gly Lys Gln Ile Ser
                85                  90                  95

Lys Gly Asn Gln Ile Arg Ile Arg Phe Val Ser Asp Glu Tyr Phe
            100                 105                 110

<210> SEQ ID NO 3
<211> LENGTH: 23
<212> TYPE: DNA
<213> ORGANISM: Artificial Sequence
<220> FEATURE:
<223> OTHER INFORMATION: PDGF-C forward primer

<400> SEQUENCE: 3
gtttgatgaa agatttgggc ttg                                            23

<210> SEQ ID NO 4
<211> LENGTH: 29
<212> TYPE: DNA
<213> ORGANISM: Artificial Sequence
<220> FEATURE:
<223> OTHER INFORMATION: PDGF-C reverse primer

<400> SEQUENCE: 4
ctggttcaag atatcgaata aggtcttcc                                      29

<210> SEQ ID NO 5
<211> LENGTH: 282
<212> TYPE: PRT
<213> ORGANISM: Homo sapiens

<400> SEQUENCE: 5

Met Ser Leu Phe Gly Leu Leu Leu Leu Thr Ser Ala Leu Ala Gly Gln
1               5                   10                  15
```

Arg Gln Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Leu Gln Leu Arg Pro Lys Thr Gly Val Arg Gly
                245                 250                 255

Leu His Lys Ser Leu Thr Asp Val Ala Leu Glu His His Glu Glu Cys
            260                 265                 270

Asp Cys Val Cys Arg Gly Ser Thr Gly Gly
        275                 280

<210> SEQ ID NO 6
<211> LENGTH: 167
<212> TYPE: PRT
<213> ORGANISM: Homo sapiens

<400> SEQUENCE: 6

Met Ser Leu Phe Gly Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

```
Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Ser Asn Arg Gly Gly Lys
145                 150                 155                 160

Ile Ile Gln Leu His Thr Ser
                165
```

MODULATION OF SMOOTH MUSCLE CELL PROLIFERATION

This application claims the benefit of U.S. provisional application Ser. No. 60/274,901, filed Mar. 9, 2001, and is the national stage application filed on Sep. 5, 2003 of the International Application No. PCT/EP02/02616 which has an international filing date of Mar. 7, 2001, each of which is incorporated herein by reference.

The present invention is concerned with modulation of smooth muscle cell proliferation and, in particular, with a novel use of vascular endothelial growth factor to enhance smooth muscle cell proliferation and to treat diseases associated with reduced smooth muscle cell proliferation.

The PDGF/VEGF growth factor family contains a number of structurally related growth factors. Members of the family contain a conserved cysteine-rich region, the cysteine knot (Sun, P. D. 1995), which forms dimers covalently linked by inter-chain disulphide bonds (Potgens et al. 1994, Andersson et al. 1992). Platelet-derived growth factor (PDGF) is mitogenic for connective tissue cells, including fibroblasts and smooth muscle cells (reviewed in Heldin et al. 1999). PDGF consists of homo- and heterodimers of distinct A and B chains, and activates two receptor tyrosine kinases, PDGFR-α and PDGFR-β. PDGF mRNA is expressed in a range of normal cell types and may be involved in tumorigenesis and other disease processes (Heldin et al. 1999). Furthermore, the PDGF-B gene is carried by transforming retroviruses as the v-sis oncogene (Devare et al., 1983), indicating that overexpression can be oncogenic.

The vascular endothelial cell growth factors are involved in neovascularisation and vascular permeability (reviewed in Ferrara & Davis-Smyth, 1997, Neufeld et al., 1999). To date five endogenous VEGFs (VEGF-A, -B, -C, -D and placenta growth factor (PLGF)) have been described. VEGF signaling is via a family of receptor tyrosine kinases (Ferrara & Davis-Smyth, 1997, Neufeld et al., 1999), though it has recently been shown that neuropilin-1 is also a receptor for some isoforms of VEGF-A (Soker et al., 1998).

VEGF-A is expressed in several normal tissues including heart, placenta and pancreas (Berse et al., 1992). It has been shown to be over-expressed in many tumors (Takahashi et al., 1995), and inhibition of VEGF-A action has been shown to cause tumor regression in animal models (Kim et al., 1993). VEGF-A has been also implicated in other disease processes involving inappropriate angiogenesis (Folkman 1995). VEGF-B mRNA expression in normal tissues overlaps with that of VEGF-A, but is also detectable in the central nervous system (Lagercrantz et al, 1998). VEGF-C is expressed at lower levels than VEGFs A and B (Lagercrantz et al, 1998), but is detectable in a range of tissues (Lee et al. 1996, Fitz et al., 1997). VEGF-D is strongly expressed in lung, heart and small intestine, and is detectable in several other tissues (Yamada et al, 1997).

A search of EST databases resulted in the identification of a new member of the VEGF/PDGF family. The identified polypeptide sequence contains an N-terminal CUB domain and a C-terminal PDGF domain, and which has been designated VASCULAR ENDOTHELIAL GROWTH FACTOR-X (VEGF-X; Patent WO 0037641; EMBL accession number AX028032). The same sequence has recently been published and shown to have PDGF activity (Li et al., 2000) and named PDGF-C and these two designations may be interchangeably used. Li et al found that the C-terminal PDGF domain of PDGF-C was active in PDGFR binding and stimulation of fibroblast proliferation, whereas the full-length PDGF-C showed no such activity. They proposed a model in which the CUB domain functions as an inhibitor of the PDGF domain: activation is via proteolysis to release the active PDGF-C.

Smooth muscle cells are important in the urethra and bladder wall to control bladder function. Increasing the number of smooth muscle cells has been demonstrated to be a therapy for stress urinary incontinence and bladder dysfunction (Yokoyama et al., 2000). The increase in cell number used as a therapy has been to directly inject smooth muscle cells (myoblasts) into the urethra and bladder wall.

On the other hand, arterial smooth muscle cell hyperplasia is known to cause various diseases and the agents that block this undesirable cellular level event could be used in drug targeted therapy for these diseases. Atherosclerosis, a disease of the large arteries, is the primary cause of heart disease and stroke. In westernized societies, it is the underlying cause of about 50% of all deaths. Atherosclerosis is a progressive disease characterized by the accumulation of lipids and fibrous elements in large arteries. The overgrowth of cells of the vessel wall, especially of the smooth muscle cells (SMCs), contributes to the pathogenesis of atherosclerosis (Lusis, A J, 2000). A treatment that could block the smooth muscle cell proliferation and migration would be sufficient to prevent intimal hyperplasia and might also contribute to the vascular healing process. In the current vascular interventional environment, high restenosis rates have increased awareness of the significance of intimal hyperplasia, a chronic structural lesion that develops after vessel wall injury, and which can lead to luminal stenosis and vessel occlusion. Intimal hyperplasia is defined as the abnormal migration and proliferation of vascular smooth muscle cells with associated deposition of extracellular connective tissue matrix (Hagen P. O., et al. 1994). Cardiac allograft arteriosclerosis is one of the major reasons for limiting long-term survival of recipients. It is characterized by intimal thickening comprised of proliferative smooth muscle cells, which may occur at the site of anastomosis because of extensive damage to the arterial wall (Suzuki J, et al. 2000). Prevention of pathological hyperproliferation of smooth muscle cells could be used to reduce the intimal hyperplasia of healing microarterial anastomoses and allograft arterial intimal hyperplasia (Robert C, et al. 1995). Arresting the growth of smooth muscle cell pericytes will help to reduce the neointimal hyperplasia induced by coronary angioplasty. Urinary bladder or kidney hypertrophy and hyperplasia are well recognized in diabetic cystopathy. The hyperproliferation of smooth muscle cells also could cause the irreversible alterations in bladder and kidney function that result from chronic and/or severe bladder outlet obstruction (Mumtaz F H, et al 2000).

It has now been surprisingly found that both the recombinant full-length VEGF-X and the CUB domain proteins exhibit a mitogenic activity on human artery smooth muscle cells in vitro, suggesting a function for the CUB domain beyond its role in maintaining latency of the PDGF domain. Therefore VEGF-X and a CUB domain which increases smooth muscle cell proliferation may be advantageous in the therapy of urinary incontinence, bladder dysfunction and dysfunction of other sphincter composed of smooth muscle cells. VEGF-X and a CUB domain can also be used during reconstruction of the pelvic floor to improve smooth muscle function.

Therefore, according to a first aspect of the present invention there is provided use of a nucleic acid molecule encoding a VEGF-X polypeptide or functional equivalents, derivatives or variants thereof in the manufacture of a medicament to stimulate smooth muscle cell proliferation in vivo or in vitro. Preferably, the sequence of the VEGF-X polypeptide is as depicted in FIG. 1(a). Also provided is the use of the CUB domain of VEGF-X, which preferably consists of the amino acid sequence from position 40 to 150 depicted in FIG. 1(a) or a functional equivalent, derivative or variant thereof, to stimulate smooth muscle proliferation in vivo or in vitro. The aforementioned polypeptides, CUB domain and nucleic acid molecules may also be used as a medicament or in the preparation of a medicament for treating urethral dysfunction, bladder dysfunction, sphincter dysfunction or other diseases or conditions associated with reduced expression of functional VEGF-X or CUB domain proteins or for pelvic floor reconstruction. In a further aspect of the invention there is provided the use of VEGF-X or the CUB domain thereof for populating matrices with smooth muscle cells for in vivo or in vitro tissue engineering applications.

The DNA molecules according to the invention may, advantageously, be included in a suitable expression vector to express VEGF-X encoded therefrom in a suitable host. Incorporation of cloned DNA into a suitable expression vector for subsequent transformation of said cell and subsequent selection of the transformed cells is well known to those skilled in the art as provided in Sambrook et al. (1989), Molecular Cloning, a Laboratory Manual, Cold Spring Harbour Laboratory Press.

An expression vector according to the invention includes a vector having a nucleic acid according to the invention operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for expression of a polypeptide according to the invention.

Such expression vectors may also be used to stimulate smooth muscle cell proliferation and also in the treatment of the diseases or conditions according to the invention including urethral dysfunction, bladder dysfunction or other diseases associated with reduced expression of functional VEGF-X protein.

The polypeptide according to the invention may be recombinant, synthetic or naturally occurring, but is preferably recombinant. Similarly, the nucleic acid sequences, according to the invention may be produced using recombinant or synthetic techniques, such as, for example, using PCR cloning mechanisms.

According to a further aspect, the present invention provides for the use of pharmaceutical compositions comprising a therapeutically effective amount of a polypeptide according to the invention, such as the soluble form of a polypeptide, or nucleic acid molecule of the present invention, or a vector incorporating said nucleic acid molecule in combination with a pharmaceutically acceptable carrier or excipient. Such carriers include, but are not limited to, saline, buffered saline, dextrose, water, glycerol, ethanol, and combinations thereof. The pharmaceutical composition according to this aspect of the invention may be used to stimulate smooth muscle cell proliferation in tissue and organs, or alternatively, to treat or prevent any of urethral, bladder or sphincter dysfunction or a dysfunction associated with aberrant endogenous activity of a VEGF-X polypeptide of the invention.

The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The protein or polypeptide (which term is used interchangeably herein) according to the invention is defined herein as including all possible amino acid variants encoded by the nucleic acid molecule according to the invention including a polypeptide encoded by said molecule and having conservative amino acid changes. Conservative amino acid substitution refers to a replacement of one or more amino acids in a protein which do not affect the function or expression of the protein. Proteins or polypeptides according to the invention are further defined herein to include variants of such sequences, including naturally occurring allelic variants which are substantially homologous to said proteins or polypeptides. In this context, substantial homology is regarded as a sequence which has at least 70%, preferably 80 or 90% and preferably 95% amino acid homology with the proteins or polypeptides encoded by the nucleic acid molecules according to the invention. "Functional equivalent" of a protein or polypeptide in accordance with the invention encompasses all the amino acid and allelic variants envisaged above exhibiting VEGF-X activity as required by the methods and uses of the invention. The protein or polypeptide according to the invention may be recombinant, synthetic or naturally occurring, but is preferably recombinant.

A protein or polypeptide in accordance with the invention as defined herein also includes bioprecursors of said protein or polypeptides. Bioprecursors are molecules which are capable of being converted in a biological process into a protein or polypeptide having the VEGF-X activity as required by the invention. The nucleic acid or protein according to the invention may be used as a medicament or in the preparation of a medicament for treating cancer or other diseases or conditions associated with expression of VEGF-X protein.

Advantageously, the nucleic acid molecule or the protein according to the invention may be provided in a pharmaceutical composition together with a pharmacologically acceptable carrier, diluent or excipient therefor.

The present invention is further directed to inhibiting VEGF-X in vivo by the use of antisense technology.

Antisense technology can be used to control gene expression through triple-helix formation of antisense DNA or RNA, both of which methods are based on binding of a polynucleotide to DNA or RNA. For example, the 5' coding portion or the mature DNA sequence, which encodes for the protein of the present invention, is used to design an antisense RNA oligonucleotide of from 10 to 50 base pairs in length. A DNA oligonucleotide is designed to be complementary to a region of the gene involved in transcription (triple-helix—see Lee et al. Nucl. Acids Res., 6:3073 (1979); Cooney et al., Science, 241:456 (1988); and Dervan et al., Science, 251: 1360 (1991), thereby preventing transcription and the production of VEGF-X.

Therefore, there is also provided by the present invention a method of treating or preventing any of atherosclerosis, neointimal hyperplasia caused by artery anastomosis or balloon catheter, postangioplasty restenosis caused by arterial stenting after percutaneous transluminal coronary angioplasty, said method comprising administering to said subject an amount of a polynucleotide molecule antisense to a nucleic acid molecule encoding VEGF-X polypeptide such as an antisense polynucleotide molecule capable of hybridizing to the nucleic acid according to FIG. 1(a) or the complement thereof under conditions of high stringency, in sufficient concentration to treat or prevent said disorders.

Conditions of high stringency generally include temperatures in excess of 30° C., typically in excess of 37° C., and preferably in excess of 45° C. Stringent salt conditions will ordinarily be less than 1000 mM, typically less than 500 mM and preferably less than 200 mM.

The composition may be adapted according to the route of administration, for instance by a systemic or an oral route. Preferred forms of systemic administration include injection, typically by intravenous injection. Other injection routes, such as subcutaneous, intramuscular, or intraperitoneal, can be used.

Alternative means for systemic administration include transmucosal and transdermal administration using penetrants such as bile salts or fusidic acids or other detergents. In addition, if a polypeptide or other compound of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1-100 mg/kg of subject. Wide variations in the needed dosage, however, are to be expected in view of the variety of compounds available and the differing efficiencies of various routes of administration.

For example, oral administration would be expected to require higher dosages than administration by intravenous injection. Variations in these dosage levels can be adjusted using standard empirical routines for optimization, as is well understood in the art.

The term "therapeutically effective amount", as used herein, means the amount of the VEGF-X, or other actives of the present invention, that will elicit the desired therapeutic effect or response or provide the desired benefit when administered in accordance with the desired treatment regimen.

A preferred therapeutically effective amount is an amount which stimulates proliferation of smooth muscle cells.

"Pharmaceutically acceptable" as used herein, means generally suitable for administration to a mammal, including humans, from a toxicity or safety standpoint.

In the present invention, the VEGF-X protein is typically administered for a sufficient period of time until the desired therapeutic effect is achieved. The term "until the desired therapeutic effect is achieved", as used herein, means that the therapeutic agent or agents are continuously administered, according to the dosing schedule chosen, up to the time that the clinical or medical effect sought for the disease or condition being mediated is observed by the clinician or researcher. For methods of treatment of the present invention, the compounds are continuously administered until the desired change in bone mass or structure is observed. In such instances, achieving an increase of smooth muscle cells is the desired objective. For methods of reducing the risk of a disease state or condition, the compounds are continuously administered for as long as necessary to prevent the undesired condition.

The combination of two or more stimulants of smooth muscle cell proliferation are also deemed as within the scope of the present invention.

"Polynucleotide" generally refers to any polyribonucleotide or polydeoxynucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA.

The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids.

"Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, PROTEINS—STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, pages. 1-12 in POSTTRANSLATIONAL COVALENT MODIFICATION OF PROTEINS, B. C. Johnson, Ed., Academic Press, New York, 1983; Selfter et al., "Analysis for protein modifications and nonprotein cofactors", Meth Enzymol (1990) 182:626-646 and Rattan et al., "Protein Synthesis: Post-translational Modifications and Aging", Ann NY Acad Sci (1992) 663:48-62).

Polypeptides comprising any of the above modifications may be described as "derivatives" of the proteins or polypeptides in accordance with the invention.

The present invention further relates to screening methods for identifying inhibitors of VEGF-X biological activity. These inhibitors include neutralizing VEGF-X antibodies, antisense VEGF-X sequences or non-protein antagonists competing with VEGF-X biological activity. Suitable antibodies can be raised against an appropriate immunogen, such as isolated and/or recombinant antigen or its portion (including synthetic molecules, such as synthetic peptides) or against a host cell which expresses recombinant antigen. In addition, cells expressing recombinant antigen, such as transfected cells, can be used as immunogens or in a screen for antibody which binds receptor (see e.g., Chuntharapai et al., J Immunol., 152.-17831-1789 (1994).

The antibody producing cell, preferably those of the spleen or lymph nodes, can be obtained from animals immunized with the antigen of interest. The fused cells (hybridomas) can be isolated using selective culture conditions, and cloned by limiting dilution. Cells that produce antibodies with the desired specificity can be selected by a suitable assay (e.g., ELISA).

Therefore, there is also provided by the present invention a method of treating or preventing any of atherosclerosis, neointimal hyperplasia caused by artery anastomosis or balloon catheter, postangioplasty restenosis caused by arterial stenting after percutaneous transluminal coronary angioplasty, said method comprising administering to said subject an amount of an antibody capable of binding to a VEGF-X polypeptide, such as in FIG. 1(a) or an epitope thereof in sufficient concentration to treat or prevent said disorders.

Anti-VEGF-X antibodies suitable for use in the present invention are characterized by high affinity binding to VEGF-X receptor. Antibodies against VEGF-X could be administered by inhalation (e.g., in an inhalant or spray or as a nebulized mist). Other routes of administration include intranasal, oral, intravenous including infusion and/or bolus injection, intradermal, transdermal (e.g., in slow release polymers), intramuscular, intraperitoneal, subcutaneous, topical, epidural, buccal, etc. routes. Other suitable routes of administration can also be used, for example, to achieve absorption through epithelial or mucocutaneous linings. Antibodies can also be administered by gene therapy, wherein a DNA molecule encoding a particular therapeutic protein or peptide is administered to the patient, e.g., via a vector, which causes the particular protein or peptide to be expressed and secreted at therapeutic levels in vivo. In addition, anti-VEGF-X antibodies can be administered together with other components of biologically active agents, such as pharmaceutically acceptable surfactants (e.g., glycerides), excipients (e.g., lactose), carriers, diluents and vehicles. Anti-VEGFX antibodies can be administered prophylactically or therapeutically to an individual prior to, simultaneously with or sequentially with other therapeutic regimens or agents (e.g., multiple drug regimens). Anti-VEGF-X antibodies that are administered simultaneously with other therapeutic agents can be administered in the same or different compositions. Anti-VEGF-X antibodies can be formulated as a solution, suspension, emulsion or lyophilized powder in association with a pharmaceutically acceptable parenteral vehicle.

The therapeutically effective amount of VEGF-X antibody can be administered in single or divided doses (e.g., a series of doses separated by intervals of days, weeks or months), or in a sustained release form, depending upon factors such as nature and extent of symptoms, and of concurrent treatment and the effect desired.

In another aspect, a screening assay for agonists and antagonists is provided which involves determining the effect of a candidate compound on the binding of VEGF-X or CUB domain polypeptide according to the invention to a VEGF-X receptor. In particular, the method involves contacting the VEGF-X receptor with a VEGF-X or a CUB domain polypeptide according to the invention and a candidate compound and determining whether VEGF-X or CUB domain polypeptide binding to the VEGF-X receptor is increased or decreased due to the presence of the candidate compound. In this assay, an increase in binding of VEGF-X or CUB domain polypeptide over the standard binding indicates that the candidate compound is an agonist of VEGF-X or CUB domain. A decrease in VEGF-X or CUB domain polypeptide binding compared to the standard indicates that the compound is an antagonist of VEGF-X or CUB domain.

The present invention may be more clearly understood from the following example and by reference to the accompanying drawings, wherein:

FIG. 1A is an illustration of cDNA sequence of PDGF-C (SEQ ID NO: 7). The predicted PDGF-C translation product is shown above the sequence (SEQ ID NO: 1), with the predicted signal sequence underlined. The location of predicted mRNA splicing events is indicated by closed triangles. The positions of the ruRNA splicing events was inferred either from direct sequencing on an isolated BAC clone or by comparison with partial BAC sequences in the EMBL database (the region from nt. 1-374 from AC0015837, release date 7 April 2000; the region from nt. 375-571 from AC009582, release date 5 Apr. 2000). No information on splicing events is currently available for the region from nt. 900-957, indicated in italics. The cryptic splice donor/acceptor sites at nt. 719/720 and 988/989 (open triangles) were inferred from variant sequences isolated by PCR. Potential N-linked glycosylation sites in the polypeptide sequence are boxed, and FIG. 1B is a variant PDGF-C protein sequence—polypeptide sequences were predicted from PCR fragments smaller than the expected size. PCR fragments covering this region were cloned and sequenced to reveal the cryptic splice donor/acceptor sites shown in FIG. 1A. PDGF-C, var 1 and var 2 sequences disclosed as SEO ID NOS 1 and 5-6, respectively.

FIG. 2 is an illustration of the comparison of PDGF-C domains with database sequences:

(A) The PDGF domain of PDGF-C was aligned with the PDGF domains of other human PDGFs and VEGFs (SEO ID NO: 8-15, respectively, in order or appearance)

(B) The CUB domain of PDGF-C was aligned with the CUB domains of BMPs and neuropilins; proteins are from *X. laevis*, mouse or chicken as indicated (SEO ID NO: 16-21, respectively, in order or appearance).

All domain sequences were taken from the PFAMA database (Rocchigiani, M. et al, (1998) Genomics 47, 204-216) and aligned using the CLUSTALW alignment program (EMBL, Heidelberg, Germany). Table 1 summarizes the results of comparisons of the regions of the proteins shown in FIG. 2. From these comparisons it is clear that the degree of similarity of the CUB domain to other database sequences is higher than that of the PDGF domain.

FIG. 3 is an illustration of the results obtained from the mRNA expression of PDGF-C:

(A) Northern blot analysis of PDGF-C mRNA distribution in tissues and cancer cell lines. Control hybridisation using a β-actin cDNA probe indicated that there were equal amounts of mRNA in each lane. The position of the PDGF-C mRNA is indicated.

(B) PCR analysis on cDNA from tissues and cancer cell lines. Control using primers designed to amplify part of the glyceraldehyde-3-phosphate dehydrogenase cDNA indicated that equivalent amounts of each cDNA were present in the amplification reactions (not shown).

FIG. 4 is an illustration of the results obtained by FISH mapping of the PDGF-C (VEGF-X) locus—an example is shown: the left panel shows the FISH signals on the human chromosome, on the right is the same mitotic figure stained with 4',6-diamidino-2-phenylindole (DAPI) to identify human chromosome 4. Also shown is a diagrammatic summary: each dot represents double FISH signals detected on chromosome 4.

FIG. 5 is an illustration of the properties of the PDGF-C recombinant proteins: (A) *Glycosylation & interchain disuiphide formation*. T.ni Hi5 cells were infected with baculovirus expressing full-length PDGF-C. Samples of baculovirus-infected insect cell medium were treated as follows: lane 1 - enzyme buffer+N-glycosidase F; lane 2 - enzyme buffer, no N-glycosidase F added; lane 3 -reduced; lane 4- nonreduced. Detection following Western blotting used anti His 6 (SEQ ID NO: 22) antibody to detect the introduced C-terminal epitope tag.

(B) Heparin binding. Purified *E.coli*-derived full-length MBP fusion protein was subjected to SDS-PAGE and the gel stained with Coomassie blue. Lane 1—loaded fraction for heparin column, lane 2 cloumn wash, lane 3—high salt elution.

(C) *Full-length and CUB domain*—Coomassie-stained SDS-PAGE of samples of PDGF-C full-length fusion protein (lane 1) and CUB domain (lane 2) produced in *E.coli*. The CUB domain was produced by refolding of insoluble material: both of the major bands at 20 and 25 kDa are detected in Western blot experiments using anti-His6 (SEO ID NO: 22) antibody so it is presumed that the 25kDa species contains uncleaved signal peptide. Molecular weight standards are indicated on the left in kDa.

Figure 6:
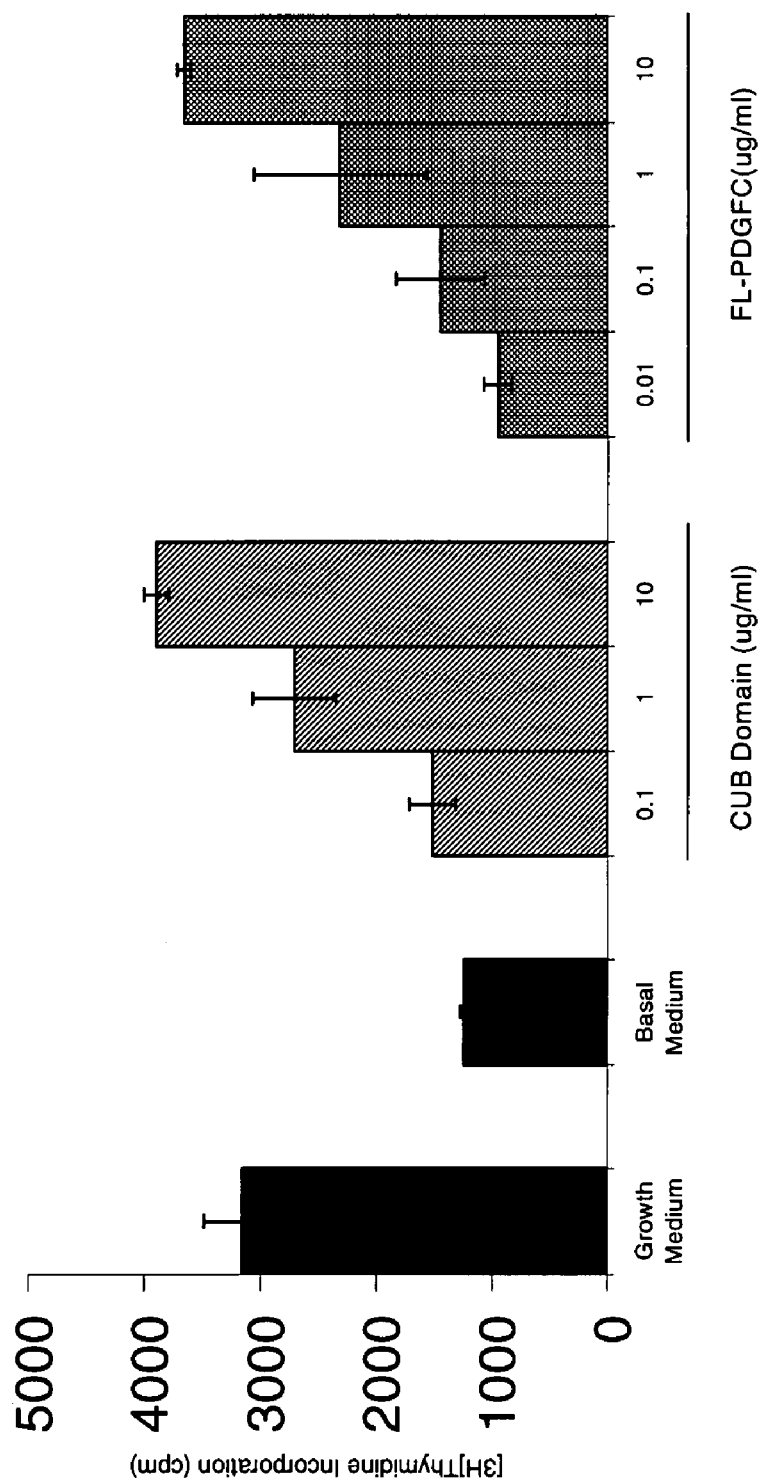

FIG. 6 is a graphic representation of the effect of PDGF-C (VEGF-X) or the PDGF-C CUB domain of human coronary artery smooth muscle cell proliferation. Cells were treated with *E. coli*-derived CUB or full-length PDGF-C proteins at the concentrations indicated.

MATERIALS AND METHODS cDNA and Partial Genomic Cloning of VEGF-X

A profile was developed (Lee et al., 1996) based on the PDGF-like domain in known VEGF sequences (VEGF-A, B, C and D), and used to search the LifeSeq™ human EST database (Incyte Genomics Inc. Palo Alto, Calif., USA), The search revealed a partial sequence of a potential novel member of the VEGF family. To extend the cDNA sequence, 5'RACE was carried out using Marathon-Readyä placenta and skeletal muscle cDNAs (Clontech, Palo Alto, Calif., USA. The full coding sequence was then amplified using standard polymerase chain reaction methods (Fitz et al., 1997). PCR fragments were cloned into vectors pCR2.1 (In-vitrogen, Carlsbad, Calif. USA) or pCR2.1-TOPO (Invitrogen, Carlsbad, Calif. USA). To determine the coding sequence, multiple clones were sequenced; also all subclones were verified by DNA sequencing. To obtain a partial genomic clone, a human genomic BAC library (Genome Systems, Inc., St Louis, Mich., USA) was screened by hybridization to oligonucleotides derived from the PDGF-C cDNA sequence. For determination of intron/exon boundaries, BAC DNA was sequenced directly using 20-mer sequencing primers based on the known cDNA sequence. BAC DNA was prepared using a Qiagen plasmid midi kit (Qiagen GmbH, Düsseldorf, Germany).

Chromosomal Localization of the VEGF-X Gene

Chromosomal mapping studies were carried out by See DNA Biotech Inc. (Toronto, Canada) using FISH analysis with a biotinylated 2.7 kb probe as described previously (Yamada et al., 1997; Gribsteor et al., 1987, Ausabel et al., 1997).

Analysis of VEGF-X mRNA Expression by Northern Blot and RT-PCR

Northern blots containing 2 µg of poly(A)+rich RNA derived from different human tissues (Clontech Laboratories; MTN™(Multiple Tissue Northern) blot, MTN™ (Multiple Tissue Northern) blot II and Cancer Cell Line MTN™ (Multiple Tissue Northern) blot) were hybridized with a a-[$^{32}$P]-dCTP random-priming labeled (Multiprime labeling kit, Roche Diagnostics) 293 bp specific PDGF-C fragment (PinAI-StuI fragment including 92 bp of the 3=end coding region and 201 bp of the 3=untranslated region of PDGF-C). The blots were hybridized overnight at 68°C. and final washes at high stringency were at 68°C. in 0.1×SSC/0.1% SDS. The membranes were autoradiographed for 1 to 3 days with intensifying screens. For RT-PCR analyses, oligonucleotide primers GTTTGATGAAAGATTTGGGCTTG (SEQ ID NO: 3) and CTGGTTCAAGATATCGAATAAGGTCT-TCC (SEQ ID NO: 4) were used for the specific PCR amplification of a 350 bp fragment from PDGF-C. PCR amplifications were performed on human TM multiple tissue cDNA (MTC™) panels (Clontech human MTC panels I and II and human Tumor MTC panel) normalized to the mRNA expression levels of six different housekeeping genes. In addition, cDNA was made from different tumor cell cultures (Caco-2 colorectal adenocarcinoma; T-84 colorectal carcinoma; MCF-7 breast adenocarcinoma; T-47D breast ductal gland carcinoma; HT1080bone fibrosarcoma; SaOS-2 osteosarcoma; SK-N-MC neuroblastoma; HepG2 hepatoblastoma; JURKAT T-cell leukemia and THP-1 myelomonocytic leukemia). For the preparation of tumor cell cDNA, cells were homogenized and total RNA prepared using the RNeasy Mini kit (Qiagen GmbH, Hilden, Germany). 1µg of total RNA was reverse transcribed using oligo(dT)$_{15}$ as a primer and 50 U of EXPAND™ (a High Fidelity enzyme blend, which consist of Taq DNA polymerase and Pwo DNA polymerase, for DNA amplification).

Reverse Transcriptase (Roche Diagnostics, Mannheim, Germany). PCR reactions with PDGF-C-specific or glyceraldehyde-3-phosphate dehydrogenase (G3PDH)-specific primers were then performed on 1 µl of this cDNA. For all cDNAs, PCR reactions with PDGF-C specific primers were performed in a total volume of 50 µl. Samples were heated to 95° C. for 30 s and cycling was performed for 30 s at 95° C. and 30 s at 68° C. for 25, 30 or 35 cycles. Control reactions using specific primers that amplify a 1 kb fragment of the housekeeping gene G3PDH were also carried out.

Expression, Purification and Detection of Recombinant Proteins

For mammalian cell expression, the full coding sequence was amplified and cloned into the vector pcDNA6/V5-His (Invitrogen, Leek, Netherlands) to add a C-terminal His$_6$ (SEQ ID NO:22) peptide tag to assist in detection and purification. For *E.coli* expression, the coding region of the predicted mature protein (Glu23-Gly345) was PCR amplified to add a C-terminal His$_6$ (SEQ ID NO: 22) tag and then cloned into the vector pMAL-p2 (New England Biolabs, Beverly, Mass., USA). The resulting MBP fusion protein was purified first on Nickel chelate resin (Ni—NTA, Qiagen GmbH, Düsseldorf, Germany) and then on amylose resin (New England Biolabs, Beverly, Mass.). The DNA sequence encoding the CUB domain fragment of PDGF-C (Glu23-Val1 71) was PCR amplified to add an N-terminal $His_6$ (SEQ ID NO: 22) tag and cloned into pET22b (Novagen, Madison, Wis.) for secretion in *E.coli*. The CUB domain protein was prepared either from the periplasm or cell-free medium of induced cultures by standard methods (Fitz et al., 1997). The protein was initially purified by precipitation with 20% saturated ammonium sulphate. After overnight dialysis against 20 mM Tris pH 8.0, 300 mM NaCl to remove ammonium sulphate, the protein was further purified on Nickel chelate resin as described above. Analysis of protein glycosylation was carried out using N-glycosidase F (Roche Molecular Biochemicals, Brussels, Belgium). Heparin Sepharose columns (Hi-Trap , Amersham Pharmacia Biotech, Uppsala, Sweden) were used according to the manufacturer=s instructions. Before use in cell-based assays, protein samples were tested for endotoxin contamination using a commercially available kit (COATEST7 Endotoxin, Chromogenix AB, Sweden).

Cell Culture

Human umbilical vein endothelial cells (HUVECs) (Clonetics, San Diego, Calif.) were maintained in EGM-2 growth medium (Clonetics, San Diego, Calif.) and human skeletal muscle cell (SkMC) (Clonetics, San Diego, Calif.) were cultured in skeletal muscle growth medium (Clonetics, San Diego, Calif.). The cells, including HCASMs (Clonetics, San Diego, Calif.), rat heart myocardium H9c2 (American Type Cell Collection, Rockville, Md.), and human neonatal dermal fibroblasts (39-SK) (American Type Cell Collection, Rockville, Md.), were maintained in Dulbecco's modified Eagle medium (DMEM) (Gibco, Gaithersburg, Md.) supplemented with 10% fetal bovine serum (FBS) (HyClone, Logan, Utah), 6 mM Hepes, 50 I.U./ml of penicillin and 50 µg/ml of streptomycin. The cells were used between passage 4-6. Human osteoblasts (MG 63) (American Type Cell Collection, Rockville, Md.) were maintained in DMEM supplemented with 10% FBS, 100 U/ml penicillin and 100 µg /ml streptomycin. Primary chondrocytes were isolated from bovine shoulders as described previously (Masure et al., 1998). Primary bovine chondrocytes were cultured in DMEM (high glucose) supplemented with 10% FBS, 10 mM HEPES, 0.1 mM non-essential amino acids, 20 µg/ml L-proline, 50 µg/ml ascorbic acid, 100 µg/ml penicillin, 100 µg/ml streptomycin and 0.25 µg /ml amphotericin B (chondrocyte growth media). All cell cultivation was carried out at 37° C. in a humidified incubator in an atmosphere of 5% $CO_2$ and 95% air.

Cell Proliferation Assay

HUVECs were trypsinized with 0.05% trypsin/0.53 mM EDTA (Gibco, Gaithersburg, Md.) and distributed in a 96-well tissue culture plate at 5,000 cells/well. Following cell attachment and monolayer formation (16 hours), cells were stimulated with various concentrations of VEGF-X in DMEM containing 0.5% to 2% FBS as indicated. For human dermal fibroblasts, the growth medium was replaced by DMEM containing 0.1% BSA with or without various concentrations of VEGF-X. For MG63, human SkMC, H9c2 or HCASMC, the medium was replaced by DMEM containing 0.5% FBS. Bovine chondrocytes were seeded in a 96-well tissue culture plate at 5,000 cells/well in a high glucose DMEM medium supplemented with 10% FBS and allowed to attach for 72 h. Medium was replaced by DMEM containing 2% BSA with or without treatments for two days. For all the cells tested, after incubation with the treatments, the culture media were replaced with 100 ml of DMEM containing 5% FBS and 3 µCi/ml of [$^3$H]-thymidine. Following pulse labeling, cells were fixed with methanol/acetic acid (3:1, vol/vol) for 1 h at room temperature. The cells were washed twice with 250 ml/well of 80% methanol. The cells were solubilized in 0.05% trypsin (100 ml/well) for 30 min then in 0.5% SDS (100 ml/well) for another 30 min. Aliquots of cell lysates (180 ml) were combined with 2 ml of scintillation cocktail and the radioactivity of cell lysates was measured using a liquid scintillation counter (Wallac 1409).

Chromosomal Localization and Intron/Exon Structure of the PDGF-C Gene

VEGF-X was localized on the long arm of human chromosome 4, region q31-q32 by FISH analysis (FIG. 2). The hybridization efficiency was ~70% for this probe. Database searches identified two genomic BAC clones which carry VEGF-X sequences (EMBL accession numbers AC009582 and AC015837). These BAC clones were derived from chromosome 4, supporting the FISH data. A BAC clone was isolated which contained the 3' part of the cDNA. By direct sequencing this clone the positions of a splicing event in the PDGF domain region of the cDNA could be deduced (nt. position 1179/1180 in FIG. 1). The position of this splice site is conserved with respect to VEGF-A and VEGF-D (Heng et al., 1993, Hagen et al., 1994). The positions of the other splice sites shown in FIG. 1 were deduced from the sequences of database BAC clones AC009582 and AC015837 described above.

Summary of Testing VEGF-X and CUB Domain

Figure 3B:
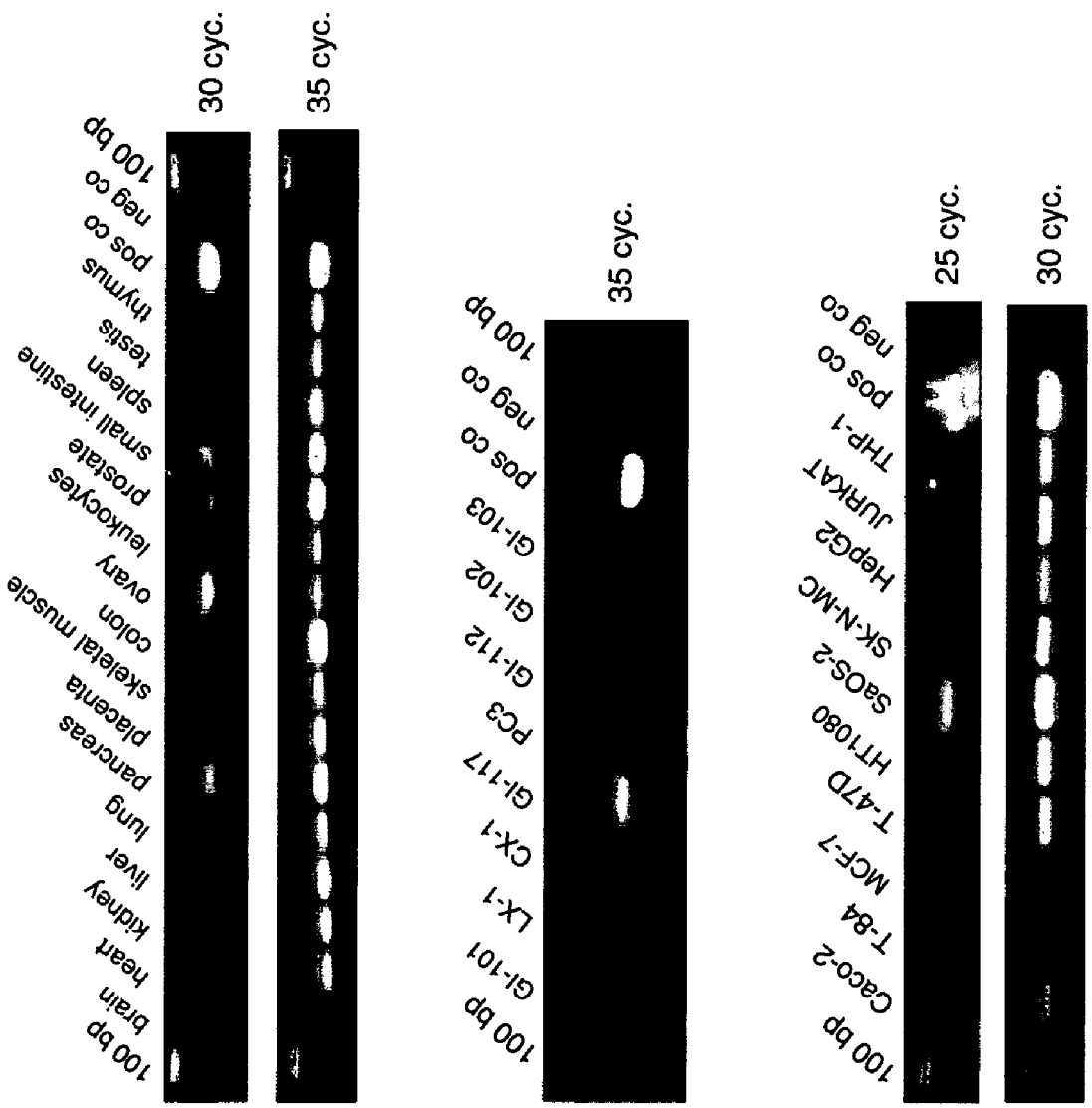

Neither the VEGF-X or CUB domain increased the proliferation of human dermal fibroblasts, human umbilical endothelial cells, bovine chondrocyte or human osteoblast cells (MG 63). However, both full-length and CUB domain constructs were able to stimulate proliferation of human coronary artery smooth muscle cells in a dose-dependent manner (FIG. 3). The optimal stimulatory concentration was in the range from 1-10 µg/ml. The effect of both the full-length or CUB domain construct, at the highest concentration tested, was four-fold over the control level (FIG. 2). We did not observe this mitogenic activity of the CUB domain on other muscle cell types, such as human skeletal muscle cells or rat heart myocardium (data not shown). Following deletion of the third cysteine or mutation to a serine residue, we found the mitogenic activity of the CUB domain on the human coronary artery smooth muscle cells was reduced to about half at the highest concentration (10 µg/ml) (data not shown).

TABLE 1

Comparison of pairwise identity and similarity for PDGF-C and related proteins

|  | % IDENTITY | % SIMILARITY |
|---|---|---|
| CUB |  |  |
| NRP_XENLA | 35 | 50 |
| NRP_MOUSE | 33 | 46 |
| NRP_CHICK | 32 | 48 |
| BMP1_XENLA | 28 | 44 |
| BMP1_HUMAN | 24 | 41 |
| PDGF |  |  |
| VEGFB | 29 | 47 |
| VEGFD | 29 | 44 |
| PDGFB | 29 | 40 |
| PDGFA | 29 | 39 |
| VEGFA | 25 | 51 |
| VEGFC | 24 | 43 |
| PLGF | 23 | 42 |
| VEGF-A vs VEGF-C | 38 | 51 |

Comparisons are between the regions of the proteins shown in FIG. 2, calculated with the Genedoc program (http://www.cris.com/~Ketchup/genedoc.shtml)

REFERENCES

Li, X., Ponten, A., Aase, K., Karlsson, L., Abramsson, A., Uutela, M., Backstrom, G., Bostrom, H., Li, H., Soriano, P., Betsholtz, C., Helding, C-H., Alitalo, K., Ostman, A. & Eriksson, U. (2000) PDGF-C is a new protease-activated ligand for the PDGF-receptor. *Nature Cell Biology* 2, 302-309.

Sun, P. D. (1995) The cystine-knot growth factor superfamily. *Annu. Rev. Biophys. Biomol. Struct.* 24, 269-291.

Potgens, A. J., Lubsen, N. H., van Altena, M. C., Vermeulen, R., Bakker, A., Schoenmakers, J. G., Ruiter, D. J. & de Waal, R. M. (1994) Covalent dimerisation of vascular permeability factor/vascular endothelial growth factor is essential for its biological activity. Evidence from Cys to Ser mutations. *J. Biol. Chem.* 269, 32879-32885.

Andersson, M., Ostman, A., Backstrom, G., Hellman, U., George-Nascimento, C., Westermark, B., & Heldin, C-H. (1992) Assignment of interchain disulphide bonds in platelet-derived growth factor (PDGF) and evidence for agoninst activity of monomeric PDGF. *J. Biol. Chem.* 267, 11260-11266.

Heldin, C-H. & Westermark, B. (1999). Mechanism of action and in vivo role of platelet-derived growth factor. *Physiological Reviews* 79, 1283-1316.

Lusis, A J. (2000) Atherosclerosis. Nature 407, 233-241.

Mumtaz F H, Shukla N, Sullivan M E, Thompson C S, Khan M A, Morgan R J, Stansby G, Mikhailidis D P. (2000). Inhibition of diabetic bladder smooth muscle cell proliferation by endothelin receptor antagonists.Urol Res 28, 254-259.

Devare, S. G., Reddy, E. P., Law, J. D., Robbins, K. C., & Aaronson, S. A. (1983). Nucleotide sequence of the simian sarcoma virus genome: demonstration that its acquired cellular sequences encode the transforming gene product p28$^{sis}$. *Proc. Natl. Acad. Sci. USA* 80, 731-735.

Ferrara, N. & Davis-Smyth, T. (1997). The biology of vascular endothelial growth factor. *Endocrine Reviews* 18, 4-25.

Neufeld, G., Cohen, T., Gengrinovitch, S. & Poltorak, Z. (1999). Vascular endothelial growth factor (VEGF) and its receptors. *FASEB J.* 13, 9-22.

Soker, S., Takashima, S., Miao, H Q., Neufeld, G. & Klagsbrun, M. (1998). Neuropilin-1 is expressed by endothelial and tumor cells as an isoform-specific receptor for vascular endothelial growth factor. *Cell* 92, 735-745.

Berse, B., Brown, L. F., Van De Water, L., Dvorak, H. & Senger, D. R. (1992). Vascular permeability factor (vascular endothelial growth factor) gene is expressed differentially in normal tissues, macrophages, and tumors. *Mol. Biol. Cell* 3, 211-220.

Takahashi, Y., Kitadai, Y., Bucana, C. D., Cleary, K. R. & Ellis, L. M. (1995). Expression of vascular endothelial growth factor and its receptor, KDR, correlates with vascularity, metastasis, and proliferation of human colon cancer. *Cancer Research* 55, 3964-3968.

Kim, N. K., Li, B., Winer, J., Armanini, M., Gillet, N., Phillips, H. S. & Ferrara, N. (1993). Inhibition of vascular endothelial growth factor-induced angiogenesis suppresses tumor growth in vivo. *Nature* 362, 841-844.

Suzuki J, Isobe M, Morishita R, Nishikawa T, Amano J and Kaneda Y. (2000). Prevention of cardiac allograft arteriosclerosis using antisense proliferating-cell nuclear antigen oligonucleotide. Transplantation 70, 398-400.

Folkman, J. (1995). Angiogenesis in cancer, vascular, rheumatoid and other disease. *Nature Medicine* 1, 27-31.

Lagercrantz, J., Farnebo, F., Larsson, C., Tvrdik, T., Weber, G. & Piehl, F. (1998). A comparative study of the expression patterns for vegf, vegf-b/vrf and vegf-c in the developing and adult mouse. *Biochem. Biophys. Acta* 1398, 157-163.

Lee, J., Gray, A., Yuan, J., Luoh, S-M, Avraham, H. & Wood, W. I. (1996). Vascular endothelial growth factor-related protein: a ligand and specific activator of the tyrosine kinase receptor Flt4. *Proc. Natl. Acad. Sci. USA* 93, 1988-1992.

Fitz, L. J., Morris, J. C., Towler, P., Long, A., Burgess, P., Greco, R., Wang, J., Gassaway, R., Nickbarg, E., Kovacic, S., Ciarletta, A., Gianotti, J., Finnerty, H., Zollner, R., Beier, D. R., Leak, L. V., Turner, K. J. & Wood, C. R. (1997). Characterization of murine Flt4 ligand/VEGF-C. *Oncogene* 15, 613-618.

Yamada, Y., Nezu, J., Shimane, M. and Hirata, Y. (1997). Molecular cloning of a novel Vascular endothelial growth factor, VEGF-D. *Genomics* 42, 483-488.

Gribskov, M., McLachlan, A. D. & Eisenberg, D. (1987). Profile analysis: Detection of distantly related proteins. *Proc. Natl. Acad. Sci. USA* 84, 4355-4358.

Ausubel, F. M., Brent, R., Kingston, R. E., Moore, D. D., Seidman, J. G., Smith, J. A. & Struhl, K. (Eds). (1997) *Current Protocols in Molecular Biology*, John Wiley and Sons, Inc.

Masure, S., Cik, M., Pangalos, M., Bonaventure, P., Verhasselt, P., Lesage, A. S., Leysen, J. E. & Gordon, R. D. (1998). Molecular cloning, expression and tissue distribution of glial-cell-derived neurotrophic factor receptor 3 (GFR-3). *Eur. J. Biochem.* 251, 622-630.

Heng, H. H. Q., Squire, J. & Tsui, L.-C. (1992) High resolution mapping of mammalian genes by in situ hybridization to free chromatin. *Proc. Natl. Acad. Sci. USA* 89, 9509-9513.

Robert C, Fouchet C, Vergely C, Pruneau D, Belichard P. (1995) Quantitative image analysis of cell proliferation after balloon catheter injury in the rabbit carotid artery. *Anal Quant Cytol Histol* 17(6):366-73.

Heng, H. H. Q. & Tsui, L.-C. (1993) Modes of DAPI banding and simultaneous in situ hybridisation. *Chromosoma* 102, 325-332.

Hagen P. O., Davies M. G., (1994) Pathobiology of intimal hyperplasia. Vr J Surg 81(9), 1254-1269.

Buschmann, M. D., Gluzband, Y. A., Grodzinsky, A. J., Kimura, J. H., and Hunziker, E. B, (1992). Chodrocytes in agarose culture synthesize a mechanically functional extracellular matrix. *J. Orthop. Res.* 10, 745-758.

Von Heijne, G., (1986) A new method for predicting signal sequence cleavage sites. *Nucleic Acids Res.* 14, 4683-4690.

Bork, P. & Beckmann, G., (1993). The CUB domain: a widespread module in developmentally regulated proteins. *J. Mol. Biol.* 231, 539-545.

Tischer, E., Mitchell, R., Hartman, T., Silva, M., Gospodarowicz, D., Fiddes, J. C. and Abraham, J. A. (1991). The human gene for vascular endothelial growth factor: Multiple protein forms are encoded through alternative exon splicing. *J. Biol. Chem.* 266, 11947-11954.

Rocchigiani, M., Lestingi, M., Luddi, A., Orlandini, M., Franco, B., Rossi, E., Ballabio, A., Zuffardi, 0. and Oliviero, S. (1998). Human FIGF: cloning, gene structure, and mapping to chromosome Xp22.1 between the PIGA and the GRPR genes. *Genomics*, 47, 207-216.

10 Romero, A., Romao, M. J., Varela, P. F., Kolln, I., Dias, J. M., Carvalho, A. L., Sanz, L., Topfer-Petersen, E. & Calvete, J. L. (1997). The crystal structures of two spermadhesins reveal the CUB domain fold. *Nature Struct.Biol.* 4, 783-788.

Paavonen, K., Horelli-Kuitunen, N., Chilov, D., Kukk, E., Pennanen, S., Kallioniemi, O. P., Pajusola, K., Olofsson, B., Eriksson, U., Joukov, V., Palotie, A. & Alitalo, K. (1996) Novel human vascular endothelial growth factor genes VEGF-B and VEGF-C localize to chromosomes 11q13 and 4q34, respectively. *Circulation* 93, 1079-1082.

Stacker, S. A., Stenvers, K., Caesar, C., Vitali, A., Domagala, T., Nice, E., Roufail, S., Simpson, R., Moritz, R., Karpanen, T., Alitalo, K. & Achen, M. (1999). Biosynthesis of vascular endothelial growth factor-D involves proteolytic processing which generates non-covalent homodimers. *J. Biol. Chem.* 274, 32127-32136.

Makinen, T., Olofsson, B., Karpanen, T., Hellman, U., Soker, S., Klagsbrun, M., Eriksson, U. & Alitalo, K. (1999). Differential binding of vascular endothelial growth factor B splice and proteolytic isoforms to neuropilin-1. *J. Biol. Chem.* 274, 21217-21222.

Bateman, A., Birney, E., Durbin, R., Eddy, S., Howe, K. L. & Sonnhammer, E. L. L. (2000). The Pfam protein families.

Yokoyama, T., Huard, J., Chancellor, M. B. World J. Urol. 18:56-61 (2000); Chancellor, M. B., Yokoyama, T., Tirney, S., Mattes, C. E., Ozawa, H., Yoshimura, N., de Groat, W. C., Huard, J. Neurol. Urodyn. 19:279-87 (2000).

The invention claimed is:

1. A method of stimulating smooth muscle cell proliferation in tissues or organs and tissue repair in a subject comprising administering to said subject an amount of a CUB domain of VEGF-X polypeptide consisting essentially of the sequence from position 40 to 150 of the amino acid sequence depicted in SEQ ID NO: 7 or a polypeptide encompassing conservative amino acid changes thereof, in sufficient concentration to stimulate smooth muscle cell proliferation, wherein conservative amino acid changes include replacement of one or more amino acids of SEQ ID NO: 7 which do not affect the function of SEQ ID NO:7; and wherein the conservative amino acid changes result in a polypeptide having at least 95% amino acid homology to the amino acid sequence depicted in SEQ ID NO:7.

2. A method of treating smooth muscle cell hypoproliferation comprising applying a therapeutically effective amount of any of a CUB domain consisting essentially of a polypeptide from position 40 to 150 of the amino acid sequence depicted in SEQ ID NO: 7 or a polypeptide encompassing conservative amino acid changes thereof, and a pharmaceutically acceptable carrier, diluent or excipient thereof, wherein conservative amino acid changes include replacement of one or more amino acids of SEQ ID NO:7 which do not affect the function of SEQ ID NO:7; and wherein the conservative amino acid changes result in a polypeptide having at least 95% amino acid homology to the amino acid sequence depicted in SEQ ID NO:7.

* * * * *